US008348915B2

(12) United States Patent
Vasic et al.

(10) Patent No.: US 8,348,915 B2
(45) Date of Patent: *Jan. 8, 2013

(54) INITIAL PRODUCT ADAPTABLE TO SERVE AS A GARMENT AND ITS METHOD OF MANUFACTURING

(75) Inventors: Dragorad Vasic, Bollebygd (SE); Helena Corneliusson, Bohus (SE); Ken Olsson, Västra Frölunda (SE)

(73) Assignee: SCA Hygiene Products AB, Göteborg (SE)

( * ) Notice: Subject to any disclaimer, the term of this patent is extended or adjusted under 35 U.S.C. 154(b) by 828 days.

This patent is subject to a terminal disclaimer.

(21) Appl. No.: 12/302,533

(22) PCT Filed: May 30, 2006

(86) PCT No.: PCT/SE2006/000632
§ 371 (c)(1),
(2), (4) Date: Nov. 26, 2008

(87) PCT Pub. No.: WO2007/139454
PCT Pub. Date: Dec. 6, 2007

(65) Prior Publication Data
US 2009/0192483 A1 Jul. 30, 2009

(51) Int. Cl.
*A61F 13/15* (2006.01)
*A61F 13/20* (2006.01)
(52) U.S. Cl. .................................. 604/385.01; 604/382
(58) Field of Classification Search .................. 604/367, 604/382, 385.01, 385.16, 385.24, 385.27
See application file for complete search history.

(56) References Cited

U.S. PATENT DOCUMENTS

| 4,940,464 A | 7/1990 | Van Gompel et al. |
| 4,990,147 A * | 2/1991 | Freeland ................. 604/385.22 |
| 5,116,662 A | 5/1992 | Morman |
| 5,422,172 A | 6/1995 | Wu |

(Continued)

FOREIGN PATENT DOCUMENTS
EP 0 432 763 A1 6/1991
(Continued)

OTHER PUBLICATIONS

International Search Report with Written Opinion of the Searching Authority (Forms PCT/ISA/210 and PCT/ISA/237) in Application No. PCT/SE2006/000631 dated Dec. 20, 2006.

(Continued)

*Primary Examiner* — Michele M Kidwell
(74) *Attorney, Agent, or Firm* — Buchanan Ingersoll & Rooney PC

(57) ABSTRACT

An initial product adaptable to form a garment such as a diaper, training pant, pull-up diaper, adult incontinence pant and diaper holder. The initial product includes a chassis for receiving the absorbent structure. The chassis includes a first lateral margin and a second lateral margin. The first and second lateral margins are joined to a central structure along a first line of joinder and a second line of joinder, respectively, the first and second lines of joinder extending substantially parallel to the longitudinal axis. The first and second lateral margins have a first end region, a second end region and a central region. The first and second lateral margins have a material which is elastically extensible in at least the longitudinal direction in the central region. Lateral edges of the lateral margins are provided by third and fourth strips of substantially inelastic material.

20 Claims, 5 Drawing Sheets

U.S. PATENT DOCUMENTS

| | | | |
|---|---|---|---|
| 5,592,690 | A | 1/1997 | Wu |
| 5,634,216 | A | 6/1997 | Wu |
| 5,861,074 | A | 1/1999 | Wu |
| 5,899,895 | A | 5/1999 | Robles et al. |
| 5,904,675 | A | 5/1999 | Laux et al. |
| 5,910,136 | A * | 6/1999 | Hetzler et al. ............ 604/367 |
| 6,417,427 | B1 | 7/2002 | Roxendal et al. |
| 6,436,083 | B1 | 8/2002 | Mishima et al. |
| 6,660,902 | B2 | 12/2003 | Widlund et al. |
| 6,685,688 | B2 | 2/2004 | Mishima et al. |
| 6,702,800 | B1 | 3/2004 | Vukos et al. |
| 6,878,647 | B1 | 4/2005 | Rezai et al. |
| 2002/0161348 | A1 | 10/2002 | Mishima et al. |
| 2003/0051804 | A1 | 3/2003 | Wood |
| 2003/0100876 | A1 * | 5/2003 | Molee ............ 604/385.22 |
| 2003/0105446 | A1 | 6/2003 | Hutson et al. |
| 2003/0109842 | A1 | 6/2003 | Louis et al. |
| 2004/0013850 | A1 * | 1/2004 | Kling ............ 428/98 |
| 2005/0256489 | A1 | 11/2005 | Sawyer et al. |

FOREIGN PATENT DOCUMENTS

| | | |
|---|---|---|
| EP | 1 064 895 A2 | 1/2001 |
| EP | 1 035 818 B1 | 4/2002 |
| JP | 3024003 U | 2/1996 |
| JP | 8-150174 A | 6/1996 |
| RU | 2 179 008 | 2/2002 |
| WO | WO 95/04654 A1 | 2/1995 |
| WO | WO 95/29810 A1 | 11/1995 |
| WO | WO 95/32093 A1 | 11/1995 |
| WO | WO 99/27876 A1 | 6/1999 |
| WO | WO 00/20206 A1 | 4/2000 |
| WO | WO 02/34182 A2 | 5/2002 |
| WO | WO 03/047488 A1 | 6/2003 |
| WO | WO 2005/110311 A1 | 11/2005 |
| WO | 2005/122985 A1 | 12/2005 |
| WO | 2006/036090 A1 | 4/2006 |

OTHER PUBLICATIONS

Vasic et al., U.S. Appl. No. 12/302,712, entitled "Garment for use with an Absorbent Structure and its Method of Manufacture" filed Nov. 26, 2008.

An English Translation of the Decision on Grant Patent for Invention issued in the corresponding Russian Patent Application No. 2008152389.

English-language translation of Notice of Reasons for Rejection issued May 31, 2011 in corresponding JP Application No. 2009-513090.

PCT/ISA/210.

PCT/ISA/237.

* cited by examiner

INITIAL PRODUCT ADAPTABLE TO SERVE AS A GARMENT AND ITS METHOD OF MANUFACTURING

TECHNICAL FIELD

The present invention relates to an initial product adaptable to serve as a garment for receiving an absorbent structure, the garment being intended to be worn around the waist of a user. Such garments are typically known as absorbent articles and include, for example, child and adult diapers, training pants, pull-up diapers, adult incontinence pants, swim pants and diaper holders for receiving an absorbent insert. The invention further relates to a method of manufacturing such an initial product.

BACKGROUND OF THE INVENTION

As well as good absorptive properties, primary requirements of absorbent articles are good fit and comfort coupled with the need to prevent leakage of any received bodily waste. To this effect, contemporary absorbent articles are provided with elastically extensible regions around the leg openings to thereby create a gusset around each leg when the article is worn. Typically, the elastically extensible regions are created by applying elastic threads under tension to a substrate and affixing the elastic threads in a stretched condition to the substrate. When the tension is released, the elastic threads contract and gather the substrate. It is also known to provide waist portions of such absorbent articles with elastically extensible regions to thereby improve the fit of the article to the user. Again, such regions may be created by the provision of elastic threads or, alternatively, elastic strips.

Similarly, the fit of pull-up type garments is enhanced if side panel regions are made from elastically extensible material.

In an attempt to improve the dynamic fit of an absorbent article, it is known from U.S. Pat. No. 5,899,895 to provide an absorbent article with a single piece of extensible material which is folded such that the extensible material extends throughout both side panels, the waist region and at least a portion of the crotch region. By suitable folding, the direction of extensibility of the material can be determined such that the material is extensible in the longitudinal direction of the article in the crotch region and in the transverse direction in the waist region. However, it is not apparent how such folding can be carried out at high production speeds.

Although many contemporary absorbent articles provide adequate fit and comfort, they demand complicated methods of manufacture. For example, the elastification of regions by means of elastic threads requires the provision of a plurality of threads and machinery which is able to apply the threads in a tensioned state to absorbent articles at high production speeds. The threads are invariably affixed to the absorbent articles by means of adhesive, something which is potentially messy and which inhibits the breathability of the finished article.

SUMMARY OF THE INVENTION

It is therefore an object of the present invention to provide an initial product, i.e. a product which may exist in a temporary state (sometimes referred to as an "intermediate product"), which itself may serve as a garment or which, after subsequent operations, may serve as a garment for receiving an absorbent structure, which initial product includes components which facilitate the mass production of such products.

To this effect, in accordance with the present invention there is provided an initial product adaptable to serve as a garment for receiving an absorbent structure, the garment being intended to be worn around the waist of a user. The initial product comprises a chassis for receiving the absorbent structure, with the chassis extending in a longitudinal direction about a longitudinal axis (L) dividing the chassis into a first lateral half and a second lateral half. The first lateral half comprises a first lateral margin and the second lateral half comprises a second lateral margin. The first and second lateral margins are joined to a central structure along a first line of joinder and a second line of joinder, respectively, with the first and second lines of joinder extending substantially parallel to the longitudinal axis (L). The chassis further extends in a transverse direction about a transverse axis (T) dividing the chassis into a first end and a second end. The chassis is delimited by a periphery comprising a first end edge at the first end and a second end edge at the second end, the first and second end edges extending substantially parallel to the transverse axis (T). The periphery further comprises a first lateral edge of the first lateral margin and a second lateral edge of the second lateral margin, the first and second lateral margins having a first end region extending from the first end edge, a second end region extending from the second end edge and a central region extending between the first and second end regions. The first and second lateral margins comprise a first strip and a second strip, respectively, of elastic material extending from the first end edge to the second end edge, which material is elastically extensible in at least the longitudinal direction in at least a portion of the central region. The first lateral edge of the first lateral margin is provided by a third strip of substantially inelastic material joined to the first strip of elastic material along a third line of joinder and the second lateral edge of the second lateral margin is provided by a fourth strip of substantially inelastic material joined to the second strip of elastic material along a fourth line of joinder, the third and fourth lines of joinder extending substantially parallel to the longitudinal axis (L).

Since, in accordance with the invention, the first and second lateral edges of the first and second lateral margins are provided by strips of substantially inelastic material, these strips serve to support the first and second strips of elastic material during the manufacturing process. This implies increased control over the manufacturing process.

In one embodiment of the invention, the first and second lateral margins further comprise fifth and sixth strips, respectively, of substantially inelastic material. The fifth and sixth strips can be arranged to serve as standing gathers when the initial product is in the form of a garment.

In a further embodiment, the elastic material of the first and second strips is elastically extensible in at least one of the first and second end regions in at least the transverse direction. Thus, the first and second lateral margins comprise a material which is elastically extensible in different directions in different regions to thereby provide the requisite fit and protection against leakage. Furthermore, the material which is elastically extensible may be substantially homogenous such that its elasticity is not dependent on adhesive being applied to the lateral margins during the assembly process of the initial product.

In one embodiment of the invention, the elastic extensibility in the longitudinal direction of the material in the central region of the first and second strips is at least 100% greater than the elastic extensibility in the transverse direction of the material in the first and/or second end regions. The elastic extensibility in the longitudinal direction in the central region may be from 90% to 350%, preferably from 150% to 300% and most preferably from 200% to 250%.

Advantageously, the material is elastically extensible in the transverse direction in both end regions.

In a preferred embodiment, the elastic material of the first and second lateral margins is elastically extensible in both the transverse and the longitudinal directions in one or more of the central region and first and second end regions.

The invention further relates to a method of manufacturing an initial product adaptable to serve as a garment for receiving an absorbent structure, the garment being intended to be worn around the waist of a user, in which the initial product comprises a chassis for receiving the absorbent structure. The chassis comprises a central structure comprising a topsheet layer and a backsheet layer, as well as first and second lateral margins joined to the central structure along first and second lines of joinder, respectively. The method comprises the steps of:

providing first and second strips of material which is or is to be made elastically extensible in at least the machine direction, the first and second strips serving as first and second strips of elastic material of the first and second lateral margins of the initial product;

feeding the first and second strips under varying tension towards a first mating station via variable speed rollers;

providing third and fourth strips of substantially inelastic material for constituting first and second lateral edges of the initial product and feeding the third and fourth strips to the first mating station;

joining the third and fourth strips to the first and second strips at the first mating station by means of third and fourth lines of joinder to produce a pair of initial united structures;

advancing the pair of initial united structures to a second mating station;

providing at least one component of the central structure and feeding the at least one component towards the second mating station, and joining the at least one component to the pair of initial united structures at the second mating station by means of the first and second lines of joinder to produce a subsequent united structure.

The reference in the method claims to the first and second strips of material which is or is to be made elastically extensible in at least the machine direction implies that the material may be initially supplied in an elastically extensible state or may subsequently be treated so as to attain that state.

Further advantageous embodiments of the initial product and its method of manufacture are detailed in the dependent claims appended hereto.

BRIEF DESCRIPTION OF THE DRAWINGS

The invention will be described in greater detail in the following by way of example only with reference to various non-limiting embodiments as depicted in the annexed drawings, in which.

DETAILED DESCRIPTION OF THE INVENTION

The invention will be described in further detail in the following with reference to the drawings in which reference number 10 generally denotes an initial product in accordance with the present invention.

Figure 1:
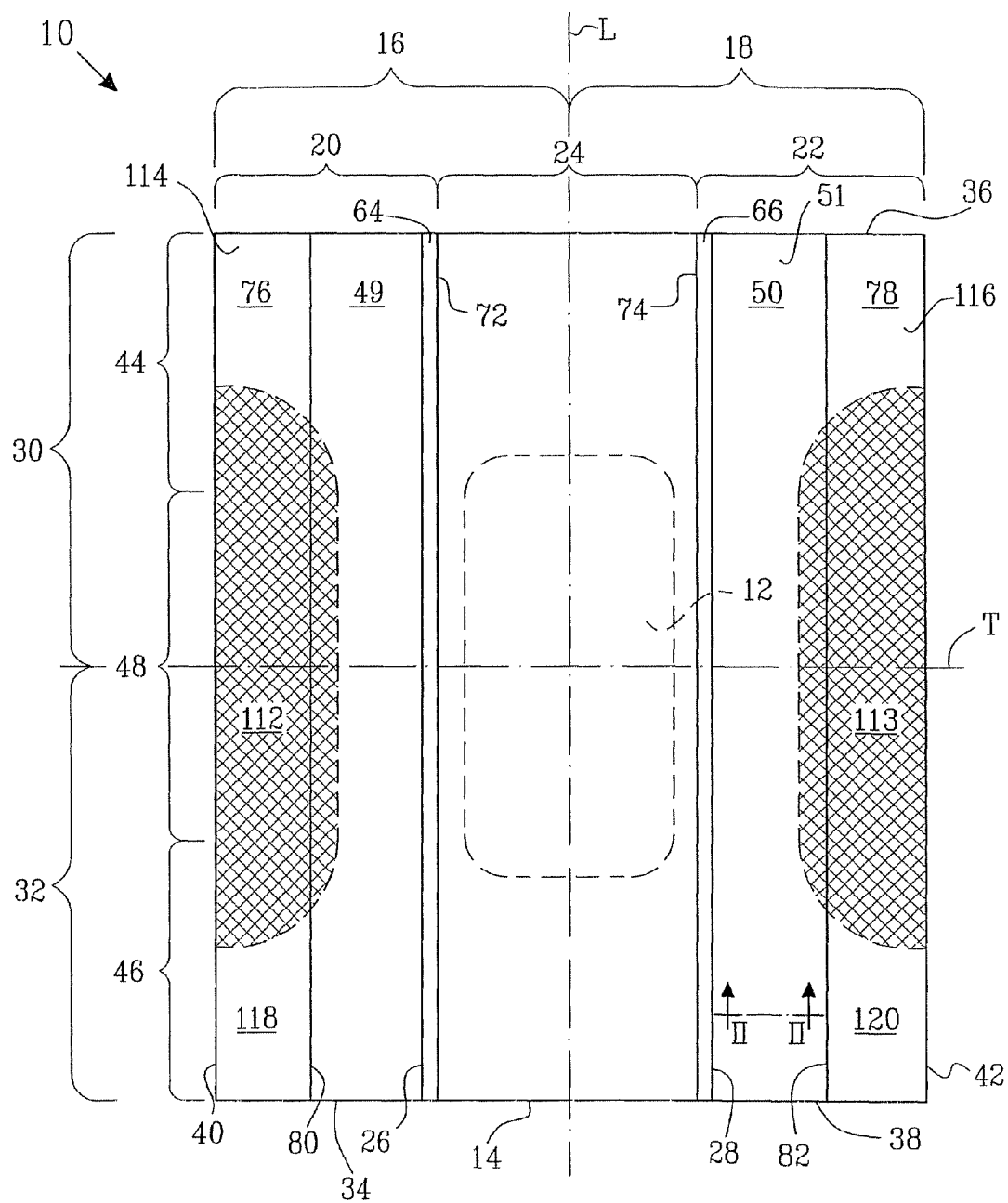
FIG. 1 is a schematic plan view of an initial product in accordance with one embodiment of the present invention in a flat, uncontracted state as seen from the body facing side.

With particular reference to FIG. 1, there is schematically shown an initial product 10 adapted to receive an absorbent structure 12. As will be described in the following, the initial product is adaptable to form a garment. In use, the garment is intended to be worn around the waist of a user. As illustrated in FIG. 1, for clarity reasons the initial product 10 is show in a laid-flat, uncontracted state. Although not illustrated, it will be understood that, when completed, the garment is provided with suitable fastening means to allow the garment to be fastened around the waist of a user.

The initial product 10 comprises a chassis 14 for receiving the absorbent structure 12. In this respect, it is to be noted that the absorbent structure 12 may either be integrally manufactured with the chassis to thereby form a unitary product, or the chassis may be adapted to receive a replaceable absorbent structure once the chassis has been manufactured. Such adaptation generally includes the provision of a pocket in the crotch region of the chassis into which a replaceable absorbent structure may be slid. The latter type of garment is generally referred to as a diaper holder.

The chassis 14 extends in a longitudinal direction about a longitudinal axis L which divides the chassis into a first lateral half 16 and a second lateral half 18. The first lateral half comprises a first lateral margin 20 and the second lateral half comprises a second lateral margin 22. The first and second lateral margins are joined in manner which will be explained later to a central structure 24 along a first line of joinder 26 and a second line of joinder 28, respectively. The first and second lines of joinder extend substantially parallel to the longitudinal axis L. In this respect, the expression "substantially parallel" means any direction having a longitudinal component which permits the first and second lateral margins to be joined to the central structure during manufacture in the machine direction. The lines of joinder 26, 28 may be continuous or intermittent and may be formed in any conventional manner, such as by ultrasonic welding or using adhesive.

The chassis 14 further extends in a transverse direction about a transverse axis T which divides the chassis into a first end 30 and a second end 32. The chassis is delimited by a periphery 34 comprising a first end edge 36 at the first end 30 and a second end edge 38 at the second end 32. Thus, the first and second end edges 36 and 38 extend substantially parallel to the transverse axis T and generally define a waist opening when the completed garment is fastened around the waist of a wearer. The periphery 34 further comprises a first lateral edge 40 of the first lateral margin 20 and a second lateral edge 42 of the second lateral margin 22.

The first and second lateral margins have a first end region 44 extending from the first end edge 36 and a second end region 46 extending from the second end edge 38. A central region 48 extends between the first and second end regions. The central region 48 is thus bisected by the transverse axis T and it is this region that will form the crotch portion of the completed garment. As such, the absorbent structure 12 is located primarily or totally in the central region. Typically, the central region 48 may be between 20% and 70%, preferably between 30% and 60% of the extension of the chassis 14 in the longitudinal direction.

In order to ensure an adequate fit and secure placement of the garment on a wearer, the first and second lateral margins 20, 22 comprise a first strip 49 and a second strip 50, respectively, of elastic material 51. The first and second strips 49, 50 extend substantially parallel to the longitudinal axis L from the first end edge 36 to the second end edge 38. The elastic material 51 is elastically extensible in at least the longitudinal direction in at least a portion of the central region 48. Preferably, the material 51 is also elastically extensible in at least a portion of, though preferably throughout, at least one of the first and second end regions 44, 46 in at least the transverse direction. In this manner, the elastic extensibility in the central region serves as leg elastic and the elastic extensibility in either or both of the first and second end regions creates extensible side panels. To ensure an even distribution of forces, the material 51 may be elastically extensible in the longitudinal direction throughout the central region.

Given that leakage is often more prevalent though leg openings than through the waist opening, in one embodiment of the invention the elastic extensibility in the longitudinal direction of the material 51 in the central region 48 is at least 100% greater than the elastic extensibility in the transverse direction of the material 51 in either or both of the first and second end regions 44, 46, with the elastic extensibility in the longitudinal direction being from 90% to 350%, preferably from 150% to 300%, and most preferably from 200% to 250%.

In this respect, it is to be noted that reference to the percentage of extensibility is indicative of the amount of extensibility over and above the contracted length of the material. Thus, by way of example, if a strip of material having a contracted length of 10.0 cm is extensible by 90%, it will reach an extended length of 19.0 cm. Furthermore, when used herein, the expression "elastic extensibility" implies that the material will undergo a plastic deformation of no more than 20%. Thus, for the example in which the 10.0 cm long strip of material is extended by 90% to 19.0 cm, it will revert to a length of no more than 12.0 cm when the force causing the extension is removed.

Experiments conducted by the applicant have shown that, in order to create a good sealing effect around the leg openings of the garment, the material 51 of the first and second lateral margins 20, 22 can be selected such that a force of at least 40 cN, preferably at least 50 cN, most preferably about 60 cN, is required to cause the material in the central region to extend 75% of its maximum value of elastic extensibility in the longitudinal direction. In one embodiment according to the invention, the material 51 in the central region 48 has an available elongation of about 120% and a force of about 60 cN is required to extend the material 75% of this value.

As mentioned previously, the elastic extensibility in the first and/or second regions in the transverse direction need not be as great as that of the elastic extensibility in the longitudinal direction in the central region and can be up to one half the elastic extensibility in the longitudinal direction. In a further embodiment of the invention, the material is elastically extensible in the transverse direction in both the first and second end regions. It is also conceivable that the material 51 be elastically extensible in the transverse direction and the longitudinal direction in one or more of the central region 48 and the first and second end regions 44, 46.

Figure 2:
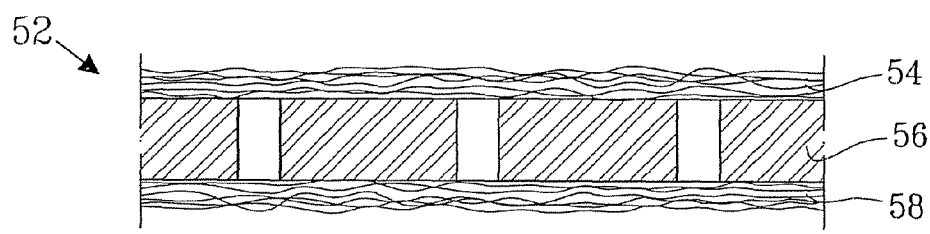
FIG. 2 is a schematic sectional view along line II-II of FIG. 1.

The material 51 may comprise various materials. As shown in FIG. 2, in one embodiment the material is an elastic web material in the form of an elastic laminate 52 comprising a first layer 54 of fibrous material and an elastic film layer 56. The elastic laminate may optionally include a second layer 58 of fibrous material, with the elastic film layer being located between the first and second layers of fibrous material. However it is understood that other types of elastic web materials may be used, such as elastic nonwoven materials, nonwoven materials which per se are inelastic, but which have been elastified by suitable means, etc. The elastic web materials may comprise one layer or two or more layers that have been laminated.

In the elastic laminate shown and described below it is preferred that the first and second layers of fibrous material 54, 58 are chosen so that they, in combination with the inner elastic film layer 56, give the material high resistance to puncture. They also provide a soft and cloth-like feel to the laminate. Examples of suitable materials are carded webs and spunbond materials. The basis weight of the fibrous material layers should be between 10 and 35 g/m$^2$, preferably between 12 and 30 g/m$^2$, more preferably between 15 and 25 g/m$^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and in this way, give the nonwoven material a higher elongation at maximum load. A mixture of polyethylene and polypropylene polymers has proved to provide good results in this respect. A mixture of fibers of different polymers is also possible.

The elastic film layer 56 may be constituted by an apertured elastic film having a basis weight between 20 and 80 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

For i.a. reasons of comfort, it is advantageous if the total basis weight of the laminate can be kept low. Thus, although a total basis weight of about 150 g/m$^2$ is acceptable, a total basis weight of 100 g/m$^2$ or less, for example no more than 90 g/m$^2$, is preferred.

The elastic laminate 52 may be manufactured according to the method disclosed in WO 03/047488, wherein one spunbond layer 54 is applied to the film 56 in a tacky state and will thus bond to the film layer, while the other spunbond layer 58 is adhesively laminated to the film layer 56, using for example a pressure sensitive hot melt adhesive.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

Elasticity in both the longitudinal direction and the transverse direction may be imparted to the laminate in the manner disclosed in, for example, WO-A-95/04654.

To provide additional wearer comfort, the elastic laminate 52 may be breathable and have a Water Vapour Transmission Rate according to ASTM E96-00 of at least 1500 g/m$^2$-24 h, preferably at least 3000 g/m$^2$-24 h.

Bi-directionally elastically extensible material which may be adapted for use in the present invention is described in the art. Examples include that which is disclosed in US-A1-2003/0105446, WO-A-95/29810, EP-A-0 432 763 and WO-A-95/32093, the contents of which are hereby incorporated by reference.

As is derivable from FIG. 2, the elastic material 51 of the first and second lateral margins may be substantially homogenous. By "substantially homogenous" it is meant that, irrespective of where in the first and second strips 49, 50 material samples of 25 mm$^2$ surface area are taken through the thickness of the material, their compositions will be effectively identical, i.e. it should not be possible to identify a particular area having a composition which differs from any other area. As a result, the material will display substantially the same properties irrespective of where on the material sample measurements are made.

In the present invention, first and second lateral margins are provided in which only a part of the margins comprises the elastically extensible material 51. Thus, in accordance with the present invention, and as is illustrated in FIG. 1, the first lateral edge 40 of the first lateral margin 20 is provided by a third strip 76 of substantially inelastic material joined to the first strip 49 of elastic material 51 along a third line of joinder 80. Similarly, the second lateral edge 42 of the second lateral margin 22 is provided by a fourth strip 78 of substantially inelastic material joined to the second strip 50 of elastic material along a fourth line of joinder 82. To facilitate manufacturing, the third and fourth lines of joinder 80, 82 extend substantially parallel to the longitudinal axis (L).

As used herein, the expression "substantially inelastic material" refers to materials having an elastic extensibility of less than 20%, preferably less than 10%, more preferably less than 5%.

In accordance with a further aspect of the present invention, the initial product can be adapted to serve as a garment by removing at least a portion of the third and fourth strips 76, 78 of substantially inelastic material. Typical such portions are shown by cross-hatching in FIG. 1 and denoted by reference numbers 112, 113, respectively. Thus, the portions 112, 113 are removed from the central region 48 of the first and second lateral margins 20, 22. This implies that a substantially inelastic first end patch 114, 116 of each of the third and fourth strips 76, 78 remains as a part of the lateral edge 40, 42 in the first end region 44 and that a substantially inelastic second end patch 118, 120 of each of the third and fourth strips 76, 78 remains as a part of the lateral edge 40, 42 in the second end region 44. These patches of substantially inelastic material provide an ideal surface on which to affix, for example, fastening tabs and/or landing zones of a garment closure system. Alternatively, in the case of a pull-up type garment, seams between side panels of the first and second end regions may be formed in the inelastic material. It is to be understood that the portions 112, 113 that are removed may also include an area of the elastic material 51.

To reduce the risk of the garment "bunching" in use, it may be advantageous if the central structure 24 of the chassis is substantially non-elastic. By allowing the central structure to carry or support the absorbent structure 12, the absorbent structure will not be directly subjected to any tensile forces in use.

Figure 3:
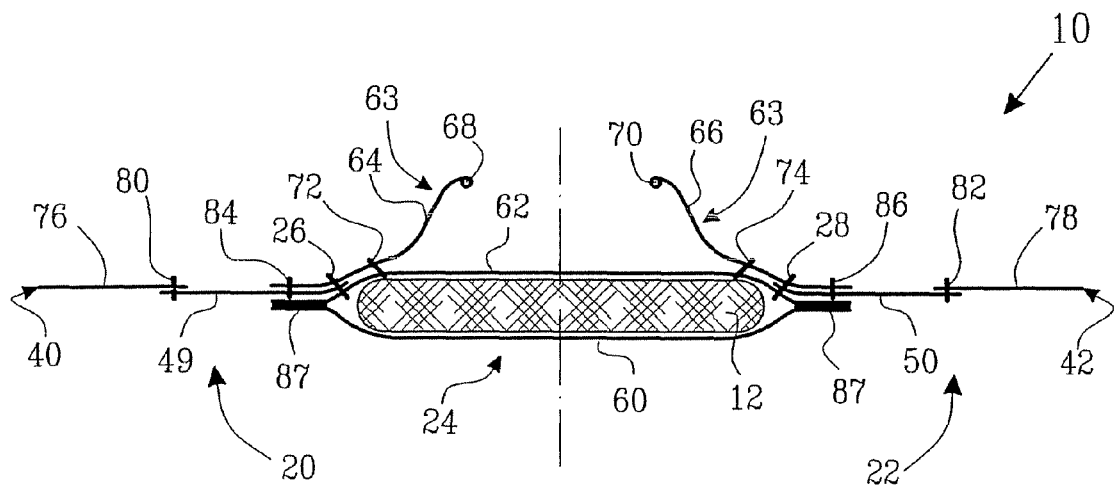
FIG. 3 is a schematic sectional view along the transverse axis of an initial product in accordance with one embodiment of the invention.

FIG. 3 is a highly schematic representation of a cross-section through an initial product 10 according to one embodiment of the invention. In this embodiment, the absorbent structure 12 is carried by the central structure 24, the central structure being constituted by a backsheet layer 60 and a topsheet layer 62, with the absorbent structure being sandwiched therebetween. The backsheet layer is advantageously of a liquid impervious material such as a thin plastic film, e.g. a polyethylene or polypropylene film, a nonwoven material coated with a liquid impervious material, a hydrophobic nonwoven material which resists liquid penetration or a laminate comprising plastic films and nonwoven materials. The backsheet layer 60 may be breathable so as to allow vapour to escape from the absorbent structure, while still preventing liquids from passing therethrough. Examples of breathable backsheet materials are porous polymeric films, nonwoven laminates from spunbond and meltblown layers, laminates from porous polymeric films and nonwovens.

The topsheet layer 62 is liquid permeable and can consist of a nonwoven material, for example spunbond, meltblown, carded, hydroentangled, wetlaid, etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet layer may further be composed of tow fibres, which may be bonded to each other in a bonding pattern, as e.g. disclosed in EP-A-1 035 818. Further examples of suitable topsheet materials are porous foams, apertured plastic films etc. The materials suited as the topsheet layer should be soft and non-irritating to the skin and intended to be readily penetrated by body fluid, e.g. urine or menstrual fluid. Any of the materials useful for the topsheet layer may be used as the substantially inelastic material of the third and fourth strips 76, 78.

The absorbent structure 12 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent structure may be varied to be suited for different uses such as for infants or for incontinent adults.

The first and second lateral margins 20, 22 are joined to the central structure 24 along first and second lines of joinder 26, 28. Depending on the various materials of the various components of the chassis, the lines of joinder may be of adhesive or created by ultrasonic welding. As illustrated in FIG. 3, the first and second lateral margins 20, 22 are joined to the topsheet layer 62 of the central structure. However, it is to be understood that the first and second lateral margins may be joined to any suitable component of the central structure.

In accordance with the present invention, the first lateral edge 40 of the first lateral margin 20 of the initial product 10 is provided by a third strip 76 of substantially inelastic, e.g. nonwoven, material joined to the first strip 49 of elastic material 51 along a third line of joinder 80. Similarly, the second lateral edge 42 of the second lateral margin 22 is provided by a fourth strip 78 of substantially inelastic, e.g. nonwoven, material joined to the second strip 50 of elastic material 51 along a fourth line of joinder 82. As explained above, in this manner, substantially non-elastic outer lateral edge regions are provided which facilitate attachment of fastening tabs. Furthermore, the substantially non-elastic material provides for better control of the elastic material during production, as well as allowing for a softer-feeling edge region on the finished product.

The garment illustrated in FIG. 3 further comprises so-called standing gathers 63 formed by fifth and sixth strips 64, 66 of substantially inelastic material. As is known per se, by providing the free end of the gathers with elastic threads 68, 70, barriers to the transmission of bodily waste in the transverse direction are created. The material of the standing gathers may be the same as for the topsheet layer 62 or it may be different. Purely by way of example, the topsheet may be a spunbond material and the standing gathers may be constituted by a meltblow material.

The optional standing gathers 63 may be formed by joining the fifth strip 64 to the first strip 49 of elastic material along a fifth line of joinder 84 and by joining the sixth strip 66 to the second strip 50 of elastic material along a sixth line of joinder 86. In FIG. 3, the fifth and sixth lines of joinder are illustrated as lying transversely outwardly of the first and second lines of joinder 26, 28, though it is to be understood that the fifth and sixth lines of joinder may be transversely inward of the first and second lines of joinder or, indeed, substantially coincident therewith. To further control movement of the standing gathers 63 when the garment is in use, the fifth and sixth strips 64, 66 may also be joined to the topsheet layer 62 transversely inwardly of the fifth and sixth lines of joinder 84, 86 by means of additional lines of joinder 72, 74.

The backsheet layer 60 and the topsheet layer 62 may be joined to each other by a peripherally extending region of joinder 87 which may comprise adhesive, for example pressure-sensitive adhesive.

Figure 4:
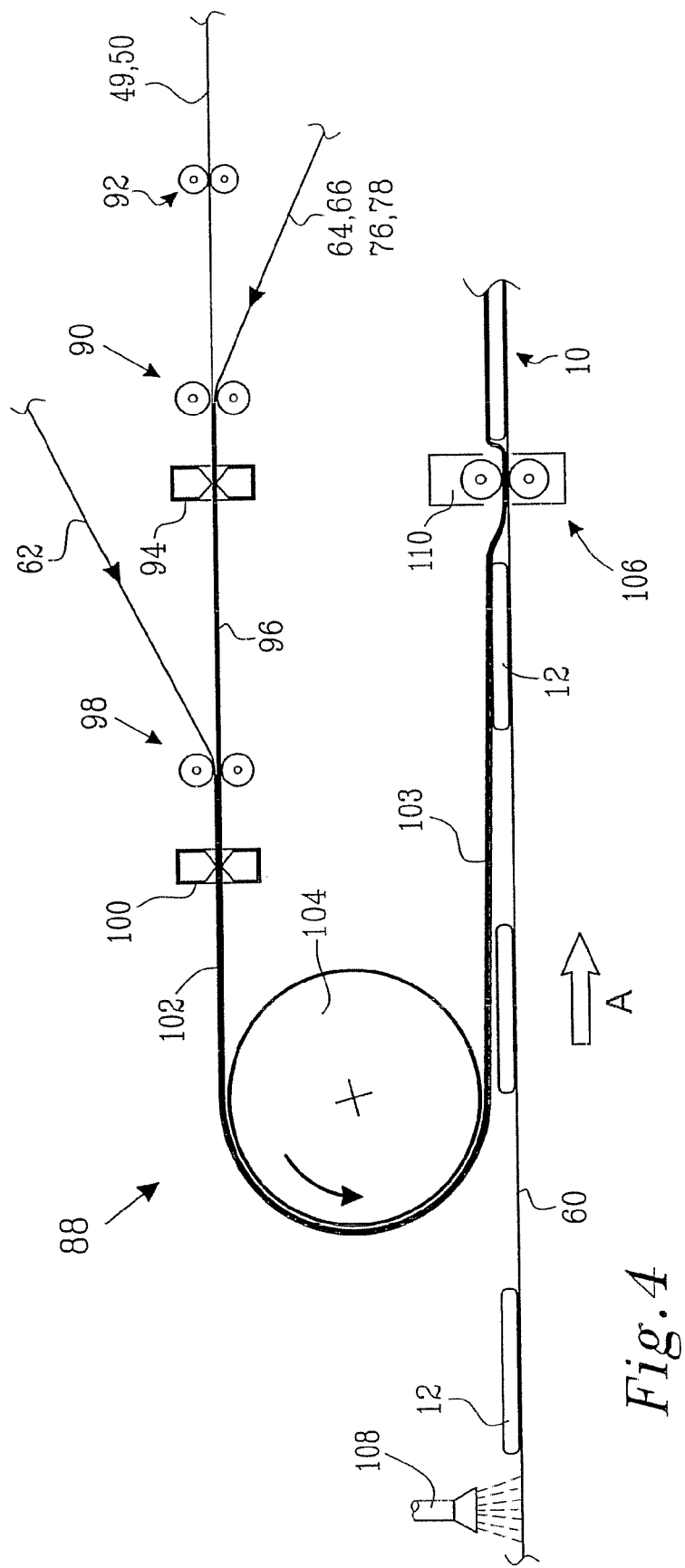
FIG. 4 is a schematic representation of a method for producing an initial product of the present invention.

The latter initial product 10 may be manufactured in accordance with a method schematically illustrated in FIG. 4. Absorbent structures 12 are carried on the backsheet layer 60 in the direction of arrow A, corresponding to the machine direction, towards receiving equipment, generally denoted by 88, for receiving the constituent components of the garment. Thus, the first and second strips 49, 50 of elastic material 51 are fed under varying tension towards a first mating station 90 via variable speed rollers 92 such that the first and second strips are extended by from 90% to 350%, preferably from 150% to 300% and most preferably from 200% to 250%, to thereby create the central regions 48 of the lateral margins 20, 22 immediately prior to being joined to the third and fourth strips 76, 78 of substantially inelastic material in the first mating station 90. Since less elasticity in the longitudinal direction is sought in the first and second end regions 44, 46 of the lateral margins, the tension is reduced immediately prior to these regions being joined to the third and fourth strips. At the first mating station, the first and second strips 49, 50 are joined to the third and fourth strips by means of e.g. ultrasonic welding provided by ultrasonic welding equipment 94 which creates the third and fourth lines of joinder 80, 82. At the same mating station, the fifth and sixth strips 64, 66 of substantially inelastic material may also be attached to the side of the first and second strips 49, 50 remote from the third and fourth strips 76, 78. Such attachment is effected by the lines of joinder denoted 84, 86 in FIG. 3. In this manner, a pair of initial united structures 96 made up of the first and second lateral margins 20, 22, i.e. comprising the first and second strips 49, 50 of elastic material, the standing gathers 63 and the third and fourth strips 76, 78 of substantially inelastic material, is produced.

At a second mating station 98, at least one component of the central structure 24 is joined to the pair of initial united structures 96 by means of e.g. ultrasonic welding provided by ultrasonic welding equipment 100 which creates the first and second lines of joinder 26, 28 shown in FIG. 3. The at least one component of the central structure 24 may be the topsheet layer 62. Either prior to, simultaneous with or subsequent to forming the first and second lines of joinder, the additional lines of joinder 72, 74 between the standing gathers 63 and the topsheet layer 62 are formed. Exiting the second mating station 98 is a subsequent united structure 102 thereby made up of the topsheet layer 62 and the first and second lateral margins 20, 22.

The subsequent united structure 102 forms an overlay package 103 and is thereafter fed towards the absorbent structure 12 and backsheet layer 60 via a feed roll 104, for example of the constant speed type, and laid over the absorbent structure and backsheet layer. The overlay package 103 is then joined to the backsheet layer 60 at a final mating station 106 to thereby sandwich the absorbent structure between the topsheet layer and the backsheet layer to form the initial product 10. As is explained earlier, the topsheet layer 62 and the backsheet layer 60 are preferably joined to each other by a peripherally extending region of joinder of adhesive material. Thus, the adhesive may be sprayed onto the backsheet at a spraying station 108 upstream of the constant speed roll 104 and activated at the final mating station 106 by means of pressure rolls 110 or the like.

The initial product 10 which emerges from the final mating station 106 is transported in the machine direction to subsequent processing stations which may include a (not shown) station at which a portion 112, 113 of the third and fourth strips 76, 78 of substantially inelastic material are removed to thereby form the garment. Advantageously, the portions 112, 113 are removed from the central region 48 of the first and second lateral margins 20, 22. It is to be understood that further processing stations which do not form a part of the present invention and are therefore not described here in further detail may be provided.

Instead of ultrasonic welding, it is to be understood that adhesive may be used at one or more of the mating stations described above in relation to FIG. 4.

In an alternative embodiment, the at least one component of the central structure 24 may comprise the entire central structure, i.e. the topsheet layer 62, the backsheet layer 60 and the absorbent structure 12 therebetween. The act of joining the pair of initial united structures 96 to the central structure 24 will create a subsequent united structure 102 which corresponds to the initial product 10.

In the above, reference has been made to elastic materials and elastic properties thereof. In the following, two test procedures will be described for assessing the elastic properties of these materials in the longitudinal direction and the transverse direction, respectively. In both procedures, a tensile tester, Lloyd LRX, able to perform cyclic movements and equipped with a printer/plotter or software presentation is used.

Procedure for Determining Retraction Forces and Available Elongation in the Longitudinal Direction:

Definitions:

The total available elongation ($T_t$) is the elongation of the sample when it is stretched from unaffected and contracted state to full length. The available elongation is expressed in % of the length of the unaffected sample.

The retraction force $P(X)$ is the elastic force in the sample when it is stretched to an available elongation of X %.

Figure 5:
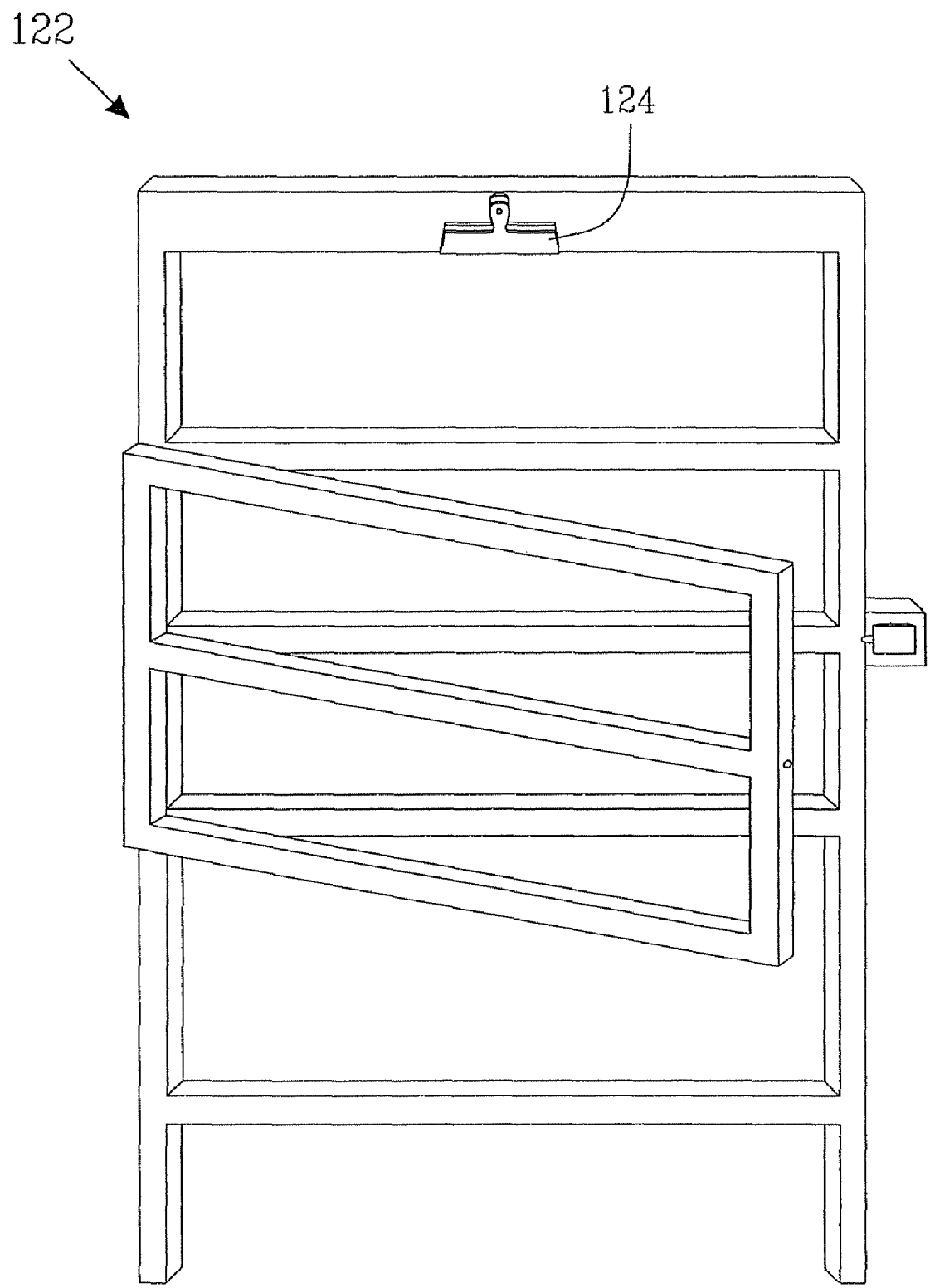
FIG. 5 is a schematic illustration of test equipment used to test elastic properties of material.

Apparatus:

Tensile tester with cross head speed of 500 mm/min and 10 N cell;

"Gate" for stretching the sample (denoted 122 in FIG. 5);

Butterfly clip with an appropriate weight for effecting desired elongation of the sample, accuracy ±1 g;
Pen and scissors;
Ruler, accuracy ±0.3 mm;
Timer, accuracy ±0.3 s.

Sample Preparation:
Cut out the first and second lateral margins 20, 22 from the product. Leave about 10 mm of the central structure 24 inward of the first and second lines of joinder 26, 28;
If the product has third and fourth strips 76, 78 forming outer lateral edge regions, these should be retained on the sample;
Remove any pulp from the central structure;
Fasten one end of the lateral margin in the gate clamp 124 and fasten the butterfly clamp with weight to the other end. The sample should be fully stretched without overstretching;
Let the weight hang freely for 15±5 s with the gate open. Close the gate and mark the distance 200 mm (or 100 mm if 200 mm is not possible);
Loosen the sample;
Allow the sample to rest for at least 30 minutes before continuing the procedure.

Procedure:
Set the distance between the clamps of the tensile tester to 50 mm (or 25 mm if 100 mm was marked in the gate);
Calibrate the tensile tester, i.e. set to zero;
Fasten the sample in the clamps so that the marks from the gate are just visible;
If the tensile tester is zeroed at the clamping length 50 mm, the sample is cycled to "max limit" 148 mm, corresponding to a clamping length of 198 mm (corresponding "max limit" 73 mm if set to zero at 25 mm);
Start the tensile tester;
Let the tensile tester carry out three cycles.

Figure 6:
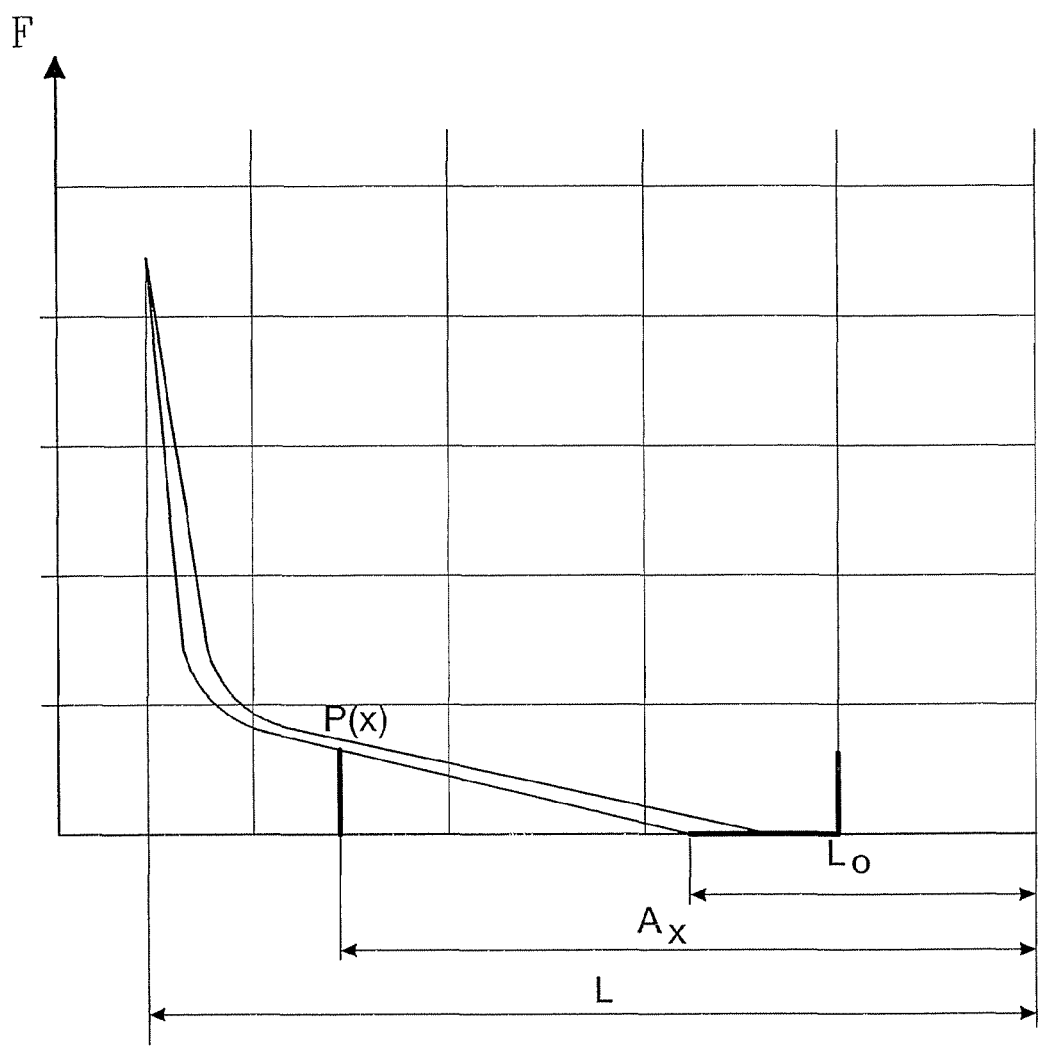
FIG. 6 is a graph of force plotted against extension and illustrating how elastic properties are to be determined.

Calculations and Expression of Results:
See FIG. 6.
$L_0$=The distance from the start point of the graph to the point on the third retraction curve where the force is equal to zero plus 50 mm (or 25 mm for the short length);
L=The length used in the gate, 198 mm (or 98 mm);
$A_X$=The distance to the point where the retraction force P(X) is read;
X=The available elongation in primary form, e.g. 20% available elongation is 1.20.
Available elongation is calculated from the formula:

$$T_i = 100 \times (L-L_0)/L_0$$

The retraction force is read from the third retraction curve at respectively available elongation according to:

$$A_X = L/X$$

The accuracy of the results is stated on available elongation in % by whole numbers ±10%, and retraction force P(X) in cN by whole numbers.

Procedure for Determining Retraction Forces and Available Elongation in the Transverse Direction:
The purpose of this procedure is to determine how an elastic material behaves at repeated load and unload cycles.

Definition:
Permanent elongation is defined as the extension of the material after it has been exposed to a repeated elongation and relaxation.

Principle:
The sample is stretched to a predetermined elongation. A cyclic movement between 0 and the predetermined elongation is performed. Desired load and unload forces are recorded. The permanent, i.e. remaining, elongation of the relaxed sample is measured.

Apparatus:
Scalpel;
Ruler, accuracy ±0.3 mm;
Pen (waterproof);
Tape;
Tensile tester with cross head speed of 500 mm/min and 10 N cell.

Sample Preparation:
The sample is prepared by cutting it to a width of 25 mm and a length that is preferably 20 mm longer than the distance between the clamps in the tensile tester;
To reduce slipping, mark the clamp distance, 50 mm, on the sample and put tape on the marks.

Procedure:
Calibrate the tensile tester;
Set the required parameters, i.e. cross head speed of 500 mm/min, clamp distance of 50 mm and preload of 0.05 N;
Place the sample in the clamps according to the marks and ensure that the sample is centered and fastened perpendicularly to the clamps;
Start the tensile tester;
Perform the predetermined number of cycles between 0 and the predetermined elongation, equal to the highest defined $1^{st}$ load force;
Before the last cycle, relax the sample for one minute then measure the permanent elongation by stretching the sample until a force of 0.1 N is detected and read the elongation.

Calculation and Expression of Results:
Desired load and unload forces are recorded. The permanent, i.e. remaining, elongation of the relaxed material is measured.

The accuracy of the results is stated to 1 decimal of values in N and in whole numbers of values in %.

The permanent elongation after relaxation of the elastic material 51 intended to be used in the present invention should be no more than 20% and is measured by the method above. Thus an elasticity of 90% is defined as that the laminate should have a permanent relaxation after elongation of no more than 20% after being exerted to an elongation of 90% in the tensile tester above. As explained previously, an elongation of 90% means an elongation to a length that is 90% longer than the initial length of the sample.

The invention has been described in the above by way of example only and various modifications will be apparent to the skilled person. For example, although the initial product according to the invention has been described having an integrated absorbent structure, it is to be understood that the initial product may instead be manufactured with a pocket for receiving a replaceable absorbent structure. Accordingly, it is to be understood that the scope and limitations of the invention are defined solely by the appended claims.

The invention claimed is:

1. An initial product adaptable to serve as a garment for receiving an absorbent structure, said garment adapted to be worn around the waist of a user, said initial product comprising:
a chassis for receiving said absorbent structure, said chassis extending in a longitudinal direction about a longitudinal axis dividing the chassis into a first lateral half and a second lateral half, said first lateral half comprising a first lateral margin and said second lateral half comprising a second lateral margin, said first and second lateral margins being joined to a central structure along a first line of joinder and a second line of joinder, respectively, said first and second lines of joinder extending substantially parallel to said longitudinal axis, said central structure comprising a backsheet layer and a topsheet layer and said absorbent structure sandwiched therebetween, wherein longitudinal terminal edges of the backsheet layer and the topsheet layer extend to the first and second lines of joinder, said chassis further extending in a transverse direction about a transverse axis dividing the chassis into a first end and a second end, said chassis being delimited by a periphery comprising a first end edge at said first end and a second end edge at said second end, said first and second end edges extending substantially parallel to said transverse axis, said periphery further comprising a first lateral edge of said first lateral margin and a second lateral edge of said second lateral margin, said first and second lateral margins having a first end region extending from said first end edge, a second end region extending from said second end edge and a central region extending between said first and second end regions, said first and second lateral margins comprising a first strip and a second strip, respectively, of elastic material extending from said first end edge to said second end edge, which material is elastically extensible in at least said longitudinal direction in at least a portion of said central region, said first lateral edge of said first lateral margin being provided by a third strip of substantially inelastic material joined to said first strip of elastic material along a third line of joinder and said second lateral edge of said second lateral margin being provided by a fourth strip of substantially inelastic material joined to said second strip of elastic material along a fourth line of joinder, said third and fourth lines of joinder extending substantially parallel to said longitudinal axis.

2. The initial product as claimed in claim 1, wherein said first and second lateral margins further comprise a fifth strip and a sixth strip, respectively, of substantially inelastic material joined at an outer end and to said first strip and said second strip, respectively, of elastic material along fifth and sixth lines of joinder, respectively, extending substantially parallel to said longitudinal axis, said fifth and sixth strips being joined to said first and second strips along edges remote from said third and fourth strips and having free inner ends such that, when serving as a garment, said fifth and sixth strips serve as standing gathers.

3. The initial product as claimed in claim 1, wherein said elastic material is elastically extensible in at least a portion of at least one of said first and second end regions in at least said transverse direction.

4. An initial product adaptable to serve as a garment for receiving an absorbent structure, said garment adapted to be worn around the waist of a user, said initial product comprising:

a chassis for receiving said absorbent structure, said chassis extending in a longitudinal direction about a longitudinal axis dividing the chassis into a first lateral half and a second lateral half, said first lateral half comprising a first lateral margin and said second lateral half comprising a second lateral margin, said first and second lateral margins being joined to a central structure along a first line of joinder and a second line of joinder, respectively, said first and second lines of joinder extending substantially parallel to said longitudinal axis, said chassis further extending in a transverse direction about a transverse axis dividing the chassis into a first end and a second end, said chassis being delimited by a periphery comprising a first end edge at said first end and a second end edge at said second end, said first and second end edges extending substantially parallel to said transverse axis, said periphery further comprising a first lateral edge of said first lateral margin and a second lateral edge of said second lateral margin, said first and second lateral margins having a first end region extending from said first end edge, a second end region extending from said second end edge and a central region extending between said first and second end regions, said first and second lateral margins comprising a first strip and a second strip, respectively, of elastic material extending from said first end edge to said second end edge, which material is elastically extensible in at least said longitudinal direction in at least a portion of said central region, said first lateral edge of said first lateral margin being provided by a third strip of substantially inelastic material joined to said first strip of elastic material along a third line of joinder and said second lateral edge of said second lateral margin being provided by a fourth strip of substantially inelastic material joined to said second strip of elastic material along a fourth line of joinder, said third and fourth lines of joinder extending substantially parallel to said longitudinal axis, wherein said elastic material is elastically extensible in at least a portion of at least one of said first and second end regions in at least said transverse direction, and wherein the elastic extensibility in said longitudinal direction of said elastic material in said at least a portion of said central region is at least 100% greater than the elastic extensibility in said transverse direction of said material in said at least a portion of said at least one of said first and second end regions.

5. An initial product adaptable to serve as a garment for receiving an absorbent structure, said garment adapted to be worn around the waist of a user, said initial product comprising:

a chassis for receiving said absorbent structure, said chassis extending in a longitudinal direction about a longitudinal axis dividing the chassis into a first lateral half and a second lateral half, said first lateral half comprising a first lateral margin and said second lateral half comprising a second lateral margin, said first and second lateral margins being joined to a central structure along a first line of joinder and a second line of joinder, respectively, said first and second lines of joinder extending substantially parallel to said longitudinal axis, said chassis further extending in a transverse direction about a transverse axis dividing the chassis into a first end and a second end, said chassis being delimited by a periphery comprising a first end edge at said first end and a second end edge at said second end, said first and second end edges extending substantially parallel to said transverse axis, said periphery further comprising a first lateral edge of said first lateral margin and a second lateral edge of said second lateral margin, said first and second lateral margins having a first end region extending from said first end edge, a second end region extending from said second end edge and a central region extending between said first and second end regions, said first and second lateral margins comprising a first strip and a second strip, respectively, of elastic material extending from said first end edge to said second end edge, which material is elastically extensible in at least said longitudinal direction in at least a portion of said central region, said first lateral edge of said first lateral margin being provided by a third strip of substantially inelastic material joined to said first strip of elastic material along a third line of joinder and said second lateral edge of said second lateral margin being provided by a fourth strip of substantially inelastic material joined to said second strip of elastic material along a fourth line of joinder, said third and fourth lines of joinder extending substantially parallel to said longitudinal axis, wherein said elastic material is elastically extensible in at least a portion of at least one of said first and second end regions in at least said transverse direction, and, wherein the elastic extensibility in said longitudinal direction of said elastic material in said central region is from 90% to 350%.

6. The initial product as claimed in claim 1, wherein the elastic material of the first and second lateral margins is selected such that in use a force of at least 20 cN is required to cause the elastic material in said central region to extend 75% of the elastic materials maximum value of elastic extensibility in said longitudinal direction.

7. The initial product as claimed in claim 6, wherein the elastic material in said central region has an available elongation of at least 120% and a force of about 60 cN is required to extend the material 75% of this value.

8. The initial product as claimed in claim 3, wherein the elastic material is elastically extensible in said transverse direction in both said first and second end regions.

9. The initial product as claimed in claim 3, wherein the elastic material is elastically extensible in said transverse direction and said longitudinal direction in one or more of said central region and said first and second end regions.

10. The initial product as claimed in claim 1, wherein the elastic material is an elastic nonwoven material or an elastic laminate comprising a first layer of elastic or non-elastic fibrous material and an elastic film layer.

11. The initial product as claimed in claim 10, wherein the elastic laminate is composed of said first layer of fibrous material, a second layer of fibrous material and said elastic film layer is located between said first and second layers of fibrous material.

12. The initial product as claimed in claim 10, wherein the first and/or the second layers of fibrous material comprise a mixture of polypropylene and polyethylene polymers.

13. The initial product as claimed in claim 10, wherein said elastic laminate comprises first and second fibrous layers of spunbond material, each having a basis weight of between 10 and 35 g/m$^2$ and an elastic film layer having a basis weight of between 20 and 80 g/m$^2$.

14. The initial product as claimed in claim 1, wherein said elastic material is breathable and has a Water Vapour Transmission Rate according to ASTM E96-00 of at least 1500 g/m$^2$-24 h.

15. The initial product as claimed in claim 1, wherein said elastic material is substantially homogenous.

16. The initial product as claimed in claim 2, wherein said third, fourth, fifth and sixth strips of substantially inelastic material are of nonwoven material.

17. The initial product as claimed in claim 1, wherein said central structure of said chassis is substantially non-elastic.

18. The initial product as claimed in claim 17, wherein said central structure carries said absorbent structure.

19. A garment for receiving an absorbent structure, said garment adapted to be worn around the waist of a user, said garment being constituted by the initial product as claimed in claim 1, in which at least a portion of said third and fourth strips of substantially inelastic material has been removed.

20. The garment as claimed in claim 19, wherein said at least a portion is removed from said central region of said first and second lateral margins.

* * * * *